United States Patent [19]

Padmapriya et al.

[11] Patent Number: 5,929,226
[45] Date of Patent: Jul. 27, 1999

[54] ANTISENSE OLIGONUCLEOTIDE ALKYLPHOSPHONOTHIOATES AND ARYLPHOSPOHONOTHIOATES

[75] Inventors: A. Padmapriya; Sudhir Agrawal, both of Shrewsbury, Mass.

[73] Assignee: Hybridon, Inc., Milford, Mass.

[21] Appl. No.: 08/436,927

[22] Filed: May 8, 1995

Related U.S. Application Data

[63] Continuation of application No. 07/919,967, Jul. 27, 1992, abandoned.

[51] Int. Cl.$^6$ .............................. C07H 21/04; C12Q 1/68; C07F 9/02
[52] U.S. Cl. ............................ 536/25.3; 435/6; 536/23.1; 536/24.31; 536/24.5; 558/122; 558/132
[58] Field of Search .............................. 514/44; 536/24.5, 536/25.3, 25.34, 25.33, 25.6, 24.31, 23.1; 558/122, 132; 935/34; 435/6, 375

[56] References Cited

U.S. PATENT DOCUMENTS

| | | | |
|---|---|---|---|
| 4,689,320 | 8/1987 | Kaji ............................................ | 514/44 |
| 4,757,055 | 7/1988 | Miller et al. ............................... | 514/44 |
| 5,003,097 | 3/1991 | Beaucage et al. ........................ | 558/129 |
| 5,015,570 | 5/1991 | Scangos et al. ............................. | 435/6 |
| 5,252,723 | 10/1993 | Bhatt ....................................... | 536/25.3 |

FOREIGN PATENT DOCUMENTS

| | | |
|---|---|---|
| 0136543 | 4/1985 | European Pat. Off. . |
| WO8908146 | 9/1989 | European Pat. Off. . |
| WO9011322 | 10/1990 | European Pat. Off. . |
| 9015065 | 12/1990 | WIPO ............................ C07H 21/00 |

OTHER PUBLICATIONS

Richards et al. (1978) *Virol.* 89:395.
Stephenson and Zamecnik (1978) *Proc. Natl. Acad. Sci.* USA 75:285–288.
Harris et al. (1980) *J. Virol.* 36:659.
Campbell et al. (1984) *Nature 311*:350.
Stec et al. (1984) *J. Am. Chem. Soc. 106*:6077–6079.
Rice et al. (1985) *Science 229*:726.
Robertson et al. (1985) *J.Virol.* 54:651.
Davison and Scott (1986) *J.Gen.Virol. 67*:2279.
Zamecnik et al (1986) *Proc. Natl. Acad. Sci.* USA 83:4143–4146.
Agrawal and Goodchild (1987) *Tet.Lett.* 28:3539–3592.
Brill and Caruthers (1987) *Tet.Lett.* 28:3205–3208.
Zurita et al. (1987) *Proc. Natl. Acad. Sci.* USA 84:2340.
Agrawal et al. (1988) *Proc. Natl. Acad. Sci.* USA 85:7079–7083.
Brill and Caruthers (1988) *Tet.Lett.* 29:1227–1230.
Roelen et al. (1988) *Nucleic Acids Res. 16*:7633–7645.
Sarin et al. (1988) *Proc. Natl. Acad. Sci.* USA 85:7448–7451.
Agrawal et al. (1989) *Proc. Natl. Acad. Sci.* USA 86:7790–7794.
Stawinski et al. (1989) *Nucleic Acids Res. Symposium* Series No. 21:47–48.
Gao et al. (1990) *Antimicrob. Agents and Chem. 34*:808.
Lebadev et al. (1990) *Tet.Lett. 31*:855–858.
Leiter et al (1990) *Proc. Natl. Acad. Sci.* USA 87:3430.
Agrawal et al. (1991) *Proc. Natl. Acad. Sci.* USA 88:7595–7599.
Stahl and Prusiner (1991) *FASEB J. 5*:2799–2807.
Storey et al. (1991) *Nucleic Acids Res. 19*:4109–4114.
Agrawal (1992) *Tibtech 10*:152–158.
K. Agrawal et al Nucl. Acids. Res. 6(9) 3009–24 ('79).
J. Goodchild et al, Bioconjugate Chem. ('90) 1(3):165–186.
W. Brill et al., Nucleosides & Nucleotides 8(5&6) ('89) 1011–4.
R. Iyer et al., J. A. C. S. 112:1253–4 '90.
Roelen et al., Tetrahedron Letts. 33(17), 2357–2360 (1992).
Helinski et al., Tetrahedron Letts 32(37), 4981–4984 (1991).
Derwent Publications Ltd., Section Ch., Week 9229, May 27, 1992, see abstract (Yodogawa Pharm. Co.).
Iyer et al., J. Org. Chem. 55, 4693–4699 (1990).
Uhlmann, E., et al. Chemical Reviews, vol. 90 (4), (Jun. '90) pp. 543–584.
B.Y. Tseng et al Cancer Gene Therapy, vol. 1, No. 1, (1994) pp. 65–71.
C.A. Stein et al. Science, vol. 261 (Aug. 20, '93) pp. 1004–1012.
J. Holz et al. Med. Cell. Biol., vol. 8#2 (Feb. 1988) pp. 963–973.
M. Cooney et al. Science, vol. 241 (Jul. 22, 1988) pp. 456–459.
C. Helene et al. Biochimie, vol. 67 ('85), pp. 777–783.
D. Tidd Anticancer Res., vol. 10 ('90) pp. 1169–1182.
L. Pauling Chem. & Eng. News, vol. 24 #10 (Mar. 25, 1946) pp. 1375–1377.
P. Weszermann et al. Biomed. Biochim. Acta, vol. 48 #1 ('89) pp. 85–93.
R. Weiss Science News, vol. 139 (Feb. 16, 1991) pp. 108–109.

*Primary Examiner*—Nancy Degen
*Assistant Examiner*—Andrew Wang
*Attorney, Agent, or Firm*—McDonnell, Boehnen Hulbert & Berghoff

[57] ABSTRACT

The invention provides improved oligonucleotides having greater resistance to nucleolytic degradation by virtue of having alkylphosphonothioate or arylphosphonothioate internucleotide linkages.

20 Claims, 2 Drawing Sheets

ANTISENSE OLIGONUCLEOTIDE ALKYLPHOSPHONOTHIOATES AND ARYLPHOSPOHONOTHIOATES

This application is a continuation of application Ser. No. 07/919,967 filed Jul. 27, 1992, now abandoned.

BACKGROUND OF THE INVENTION

1. Field of the Invention

The invention relates to antisense oligonucleotides. More particularly, the invention relates to oligonucleotides having modified internucleotide linkages that render the oligonucleotides more resistant to nucleolytic degradation.

2. Summary of the Related Art

Synthetic oligonucleotides have become important tools in basic scientific research. Recently, synthetic oligonucleotides have been successfully used in the area of regulation of gene expression, which has laid the foundation for a novel therapeutic approach, known as antisense oligonucleotide therapy, for the treatment of various virus infections and disorders of gene expression. Several investigators have demonstrated the ability of oligonucleotides to inhibit virus propagation and to modulate gene expression in vitro.

Zamecnik and Stephenson, Proc. Natl. Acad. Sci. USA 75: 285–288 (1978) discloses specific inhibition of Rous Sarcoma Virus replication in infected chicken fibroblasts by a 13-mer synthetic oligodeoxynucleotide that is complementary to part of the viral genome.

Zamecnik et al., Proc. Natl. Acad. Sci. USA 83: 4143–4146 (1986) discloses inhibition of replication and expression of human immunodeficiency virus (HIV-1, then called HTLV-III) in cultured cells by synthetic oligonucleotide phosphodiesters complementary to viral RNA.

Recent studies have shown that oligonucleotides act with greater efficacy in the antisense approach when the oligonucleotides are modified to contain artificial internucleotide linkages that render the oligonucleotides resistant to nucleolytic degradation. These studies have involved the use of a variety of artificial internucleotide linkages. The most well studied artificial internucleotide linkages have been methylphosphonate, phosphorothioate and various phosphoramidate internucleotide linkages.

Sarin et al., Proc. Natl. Acad. Sci. USA 85: 7448–7451 (1988) teaches that oligodeoxynucleoside methylphosphonates are more active as inhibitors of HIV-1 than conventional oligodeoxynucleotides.

Agrawal et al., Proc. Natl. Acad. Sci. USA 85: 7079–7083 (1988) teaches that oligonucleotide phosphorothioate and various oligonucleotide phosphoramidates are more effective at inhibiting HIV-1 than conventional oligodeoxynucleotides.

Agrawal et al., Proc. Natl. Acad. Sci. USA 86: 7790–7794 (1989) discloses the advantage oligonucleotide phosphorothioates in inhibiting HIV-1 in early and chronically infected cells.

Gao et al., Antimicrob. Agents and Chem. 34: 808 (1990) discloses inhibition of HSV by oligonucleotide phosphorothioates.

Storey et al., Nucleic Acids Res. 19: 4109 (1991) discloses inhibition of HPV by oligonucleotide phosphorothioates.

Leiter et al., Proc. Natl. Acad. Sci. USA 87: 3430 (1990) discloses inhibition of influenza virus by oligonucleotide phosphorothioates.

Unfortunately, oligonucleotide phosphorothioates increase resistance to nucleolytic degradation but do not provide complete resistance in vivo.

Agrawal et al., Proc. Natl. Acad. Sci. USA 88: 7595–7599 (1991) teaches that oligonucleotide phosphorothioates are extensively degraded from the 3' end in mice.

The greater efficacy in the antisense approach of modified oligonucleotides having artificial internucleotide linkages that render the oligonucleotides resistant to nucleolytic degradation underscores the importance of developing oligonucleotides having new artificial internucleotide linkages that provide even greater resistance to nucleolytic degradation. Non-ionic oligonucleotides are of particular interest, because of their improved uptake by cells. A possible candidate as a new and useful non-ionic artificial internucleotide linkage is the alkylphosphonothioate linkage. However, no procedure has been developed to allow the incorporation of alkylphosphonothioate internucleotide linkages into synthetic oligonucleotides. Previous attempts have been limited to solution phase synthetic efforts to produce dinucleotides containing a methylphosphonothioate internucleotide linkage.

Brill and Caruthers, Tet. Lett. 28: 3205–3208 (1987) and Tet. Lett. 29: 1227–1230 (1988) disclose an approach using methyl phosphonothioic dichloride to produce dinucleotides having a methylphosphonothioate internucleotide linkage in 56% yield.

Roelen et al., Nucleic Acids Res. 16: 7633–7645 (1988) discloses a solution phase approach, using a reagent obtained in situ by treating methylphosphonothioic dichloride with 1-hydroxy-6-trifluoromethyl benzotriazole to introduce a methylphosphonothioate internucleotide linkage into a dinucleotide in 60–70% yield, and produces a hexamer containing the linkage by two consecutive condensations of dimers.

Lebadev et al., Tet. Lett. 31: 855–858 (1990) discloses a solution phase approach to produce dinucleotides containing a stereospecific methylphosphonothioate internucleotide linkage in 50–60% yield.

Stawinski et al., Nucleic Acids Res. Symposium Series No. 21: 47–48 (1989), discloses synthesis of nucleoside H-phosphonothioates and nucleoside methylphosphonothioates.

To use alkylphosphonothioate artificial internucleotide linkages in an antisense approach, however, it is necessary to incorporate such internucleotide linkages into oligonucleotides, rather than dinucleotides. Unfortunately, the related art is devoid of any feasible method for doing this.

Synthesis of oligonucleotides having other non-ionic artificial internucleotide linkages is known in the art. For example, Agrawal and Goodchild, Tet. Lett. 28: 3539–3592 (1987) discloses a nucleoside methylphosphonamidite approach in a standard amidite coupling cycle to produce oligonucleotides having methylphosphonate internucleotide linkages. However, this reference contains no suggestion concerning the synthesis of oligonucleotide methylphosphonothioates or alkylphosphonothioates.

Several references report methods for oxidative sulfurization of oligonucleotides. For example, Stac et al., J. Am. Chem. Soc. 106: 6077–6079 (1984) discloses sulfurization of oligonucleotide phosphite triesters using elemental sulfur in a carbon disulfide:pyridine:triethylamine solution. Beaucage et al., U.S. Pat. No. 5,003,097 (1991) discloses a method for sulfurization of oligonucleotides using 3H-1,2-Benzodithiol-3-one 1,1-dioxide. However, these references demonstrate oxidative sulfurization of natural phosphodiester internucleotide linkages in oligonucleotides and do not demonstrate oxidative sulfurization of an intermediate methylphosphite linkage to generate methylphosphonothiate.

There is, therefore, a need for methods to produce additional modified oligonucleotides having non-ionic artificial internucleotide linkages, such as alkylphosphonothioate or arylphosphonothioate linkages. Ideally, such methods will be adaptable to standard methods for synthesizing oligonucleotides, thereby allowing convenient assembly of the modified oligonucleotides and of chimeric oligonucleotides having varied internucleotide linkages.

BRIEF SUMMARY OF THE INVENTION

In a first aspect, the invention provides a method for synthesizing oligonucleotides having alkylphosphonothioate or arylphosphonothioate internucleotide linkages. The method of the invention is readily adaptable to standard amidite coupling cycles, thereby allowing convenient assembly of oligonucleotides. This feature of the invention also allows great flexibility in the types of oligonucleotides that can be synthesized, since different internucleotide linkages can be introduced in various coupling cycles.

Thus, in a second aspect, the invention provides a method for synthesizing chimeric oligonucleotides having one or more alkylphosphonothioate or arylphosphonothioate internucleotide linkage at any position or positions within the oligonucleotide or at either or both ends, in addition to having natural or other artificial internucleotide linkages at other positions in the oligonucleotide.

In a third aspect, the invention provides oligonucleotides having one or more alkylphosphonothioate or arylphosphonothioate internucleotide linkage at any selected position or positions within the oligonucleotide and/or at either end or both ends. These oligonucleotides according to the invention are more resistant to nucleolytic degradation than oligonucleotides that are known in the art.

In a fourth aspect, the invention provides chimeric oligonucleotides having alkylphosphonothioate or arylphosphonothioate internucleotide linkages at some positions in the oligonucleotide and natural or other artificial internucleotide linkages at other positions in the oligonucleotide. These chimeric oligonucleotides can overcome the difficulties of limited solubility and duplex stability, which are otherwise inherent in oligonucleotides having only non-ionic internucleotide linkages.

The improved properties of the oligonucleotides according to the invention, such as greater resistance to nucleolytic degradation than known oligonucleotides and greater solubility and duplex stability in some embodiments than known non-ionic oligonucleotides, render the oligonucleotides according to the invention particularly useful both in basic scientific applications for studying modulation of gene regulation, and in the antisense oligonucleotide therapeutic approach to treating virus and pathogen infections as well as disorders of gene expression.

DETAILED DESCRIPTION OF THE PREFERRED EMBODIMENTS

The invention relates to oligonucleotides that are useful in the antisense oligonucleotide therapeutic approach. More particularly, the invention relates to oligonucleotides having modified internucleotide linkages that render the oligonucleotides more resistant to nucleases.

Figure 2:
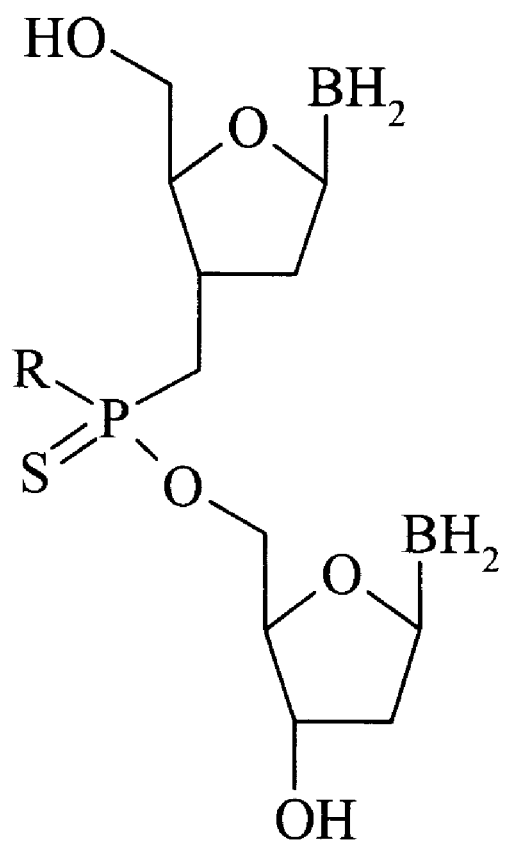
FIG. 2 shows an alkylphosphonothioate or arylphosphonothioate internucleotide linkage. R=an alkyl group having one to seven carbon atoms, or an aryl group, either of which may be unsubstituted or substituted, e.g., with halo, hydroxy, trifluoromethyl, cyano, nitro, acyl, acyloxy, alkoxy, carboxyl, carbalkoxyl, or amino groups.

In a first aspect, the invention provides a method for synthesizing oligonucleotides having alkylphosphonothioate or arylphosphonothioate internucleotide linkages. Such linkages are illustrated in FIG. 2. By using the method of the invention, such alkylphosphonothioate or arylphosphonothioate internucleotide linkages can be introduced at any position within the oligonucleotide. Thus, oligonucleotides can be produced that have one or more alkylphosphonothioate or arylphosphonothioate internucleotide linkage at or near the 3' end of the oligonucleotide, at or near the 5' end of the oligonucleotide, centrally located within the oligonucleotide, or at any combination of such positions. For purposes of the invention, near the 3' or 5' end is intended to mean within 4 nucleotides of such end, and centrally located is intended to refer to any location within the oligonucleotide other than at or near the 3' or 5' end of the oligonucleotide.

The method of synthesizing oligonucleotides according to the invention is compatible with both H-phosphonate and phosphoramidate approaches to synthesizing oligonucleotides.

This feature provides an additional advantage, since it allows the synthesis of oligonucleotides having alkylphosphonothioate or arylphosphonothioate internucleotide linkages in addition to any other internucleotide linkage that can be introduced by using the H-phosphonate or phosphoramidate approach, or variations thereof. Such other internucleotide linkages include, but are not limited to phosphodiester, phosphorothioate, phosphorodithioate, alkylphosphonate internucleotide linkages, phosphotriesters, phosphoramidate, ketone, sulfone, carbonate and thioamidate linkages.

Thus, in a second aspect, the invention provides a method for synthesizing chimeric oligonucleotides having one or more alkylphosphonothioate or arylphosphonothioate internucleotide linkage at any selected position or positions within the oligonucleotide, in addition to having other types of internucleotide linkages at other positions within the oligonucleotide.

Figure 1:
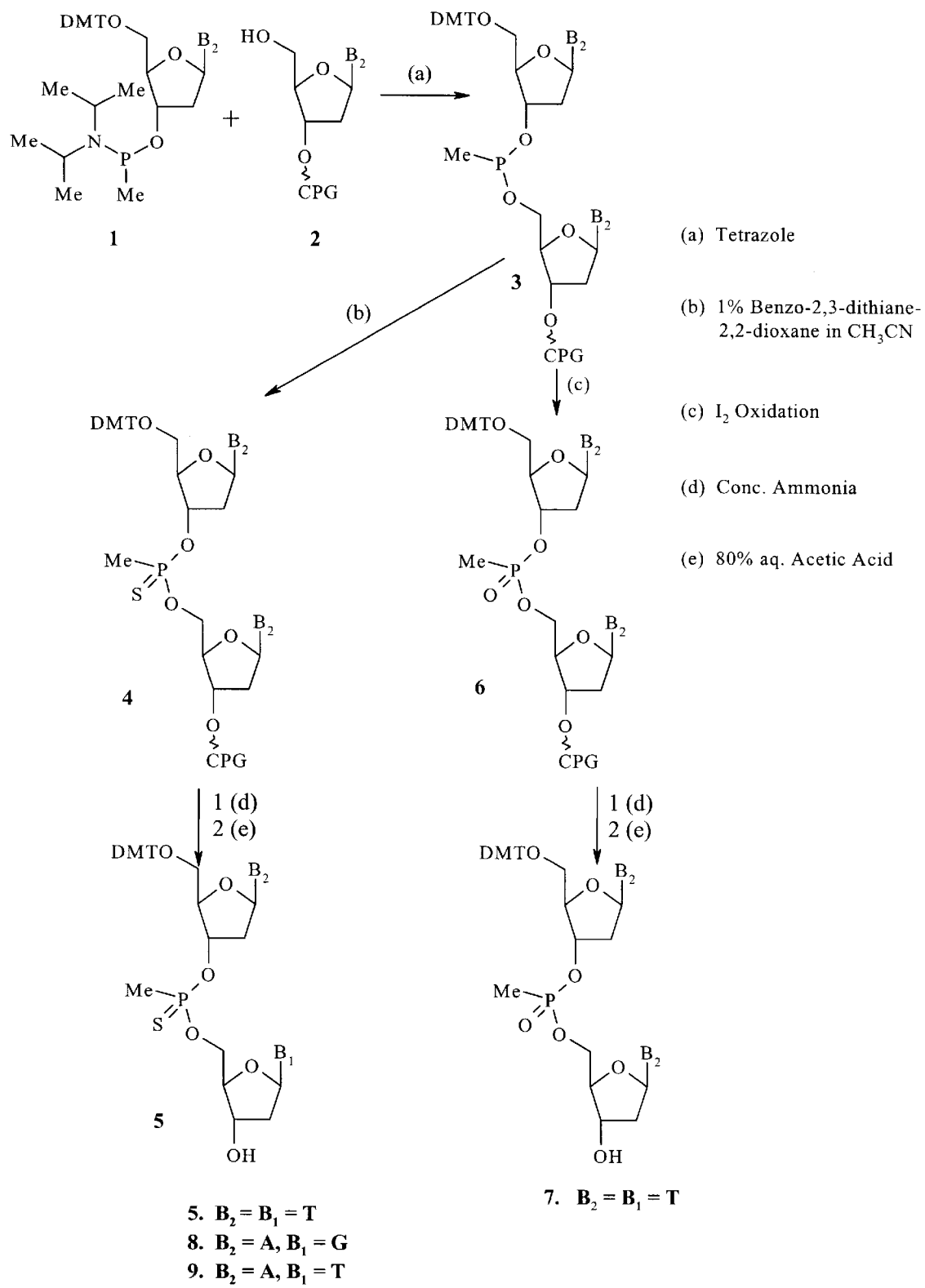
FIG. 1 illustrates the steps involved in the synthesis of oligonucleotide methylphosphonothioates in a preferred embodiment of the method of the invention.

According to either of these first two aspects of the invention, the method of the invention for synthesizing oligonucleotides having alkylphosphonothioate or arylphosphonothioate internucleotide linkages comprises the following steps: (a) coupling together two nucleosides via an alkylphosphite or arylphosphite linkage, and (b) oxidatively thiolating the alkylphosphite linkage to produce an alkylphosphonothioate or arylphosphonothioate linkage. FIG. 1 illustrates a preferred embodiment of this method, in which a methylphosphite linkage is oxidatively thiolated to form a methylphosphonothioate linkage. Other substituted or unsubstituted alkylphosphonate or arylphosphonate linkages can be similarly prepared, by replacing the phosphate-bound methyl group shown in compound 1 of FIG. 1 with such a substituted or unsubstituted alkyl or aryl group. In a preferred embodiment, the coupling of step (a), above, is carried out using β-cyanoalkylphosphoramidites and a standard amidite coupling cycle (See, e.g., Agrawal and Goodchild, Tet. Lett. 28: 3539–3592 (1987)). In another preferred embodiment, the oxidative thiolation of step (b), above, is carried out by treating the alkylphosphite or arylphosphite linkage with Beaucage reagent (3H-1,2-benzodithiole-2-one) in an appropriate solvent. In all embodiments of the method according to the invention, the coupling together of other nucleotides, i.e., nucleotides not joined by an alkylphosphonothioate or arylphosphonothioate linkage, may be carried out by any known coupling approach, preferably by an H-phosphonate approach (See U.S. Pat. No. 5,149,798; Ser. No. 07/334,679; allowed on Mar. 19, 1992; the teachings of which are hereby incorporated by reference) or by a conventional phosphoramidate approach.

The essential steps described above for producing nucleotides coupled by an alkylphosphonothioate or arylphosphonothioate linkage can be repeated to produce an oligonucleotide having exclusively alkylphosphonothioate or arylphosphonothioate linkages, or preferably can be varied with other coupling steps to produce oligonucleotides having alkylphosphonothioate or arylphosphonothioate linkages only at defined positions. Thus, to produce oligonucleotides having alkylphosphonothiate or arylphosphonothioate linkages only at or near the 3' end, coupling of nucleotides together via alkylphosphite or arylphosphite linkages will be undertaken initially, followed by oxidation with Beaucage reagent and the addition of other nucleotides or nucleotide analogs via, e.g., H-phosphonate or phosphoramidate coupling cycles. In contrast, if alkylphosphonothioate or arylphosphonothioate linkages are desired at or near the 5' end of the oligonucleotide, then initial couplings will involve, e.g., H-phosphonate or phosphoramidate chemistry to produce whatever internucleotide linkages are desirable. Then, at the point where alkylthiophosphonate or arylphosphonothioate linkages are desired, nucleosides will be linked together via alkylphosphite or arylphosphite linkages and oxidative thiolation will be undertaken.

Those skilled in the art will recognize that steps (a) and (b), as described above, can be introduced at any point in an oligonucleotide synthesis scheme, thereby allowing the incorporation of alkylthiophosphonate or arylphosphonothioate linkages at any position within the oligonucleotide. In addition, since the above steps (a) and (b) can be incorporated into any synthesis scheme, any other well-known internucleotide linkage can be incorporated into the alkylthiophosphonate or arylphosphonothioate linkage-containing oligonucleotide. Examples of such well known linkages, for which conventional synthesis schemes are known, include alkylphosphonate, phosphodiester, phosphotriester, phosphorothioate, phosphorodithioate, phosphoramidate, ketone, sulfone, carbonate and thioamidate linkages.

In a third aspect, the invention provides improved oligonucleotides for use in the antisense oligonucleotide therapeutic approach. For purposes of the invention, the term oligonucleotide includes polymers of ribonucleotides, deoxyribonucleotides, or both, with ribonucleotide and/or deoxyribonucleotide monomers being connected together via 5' to 3' linkages which may include any of the linkages that are known in the antisense oligonucleotide art. In addition, the term oligonucleotide includes such molecules having modified nucleic acid bases and/or sugars, as well as such molecules having added substituents, such as diamines, cholesteryl, or other lipophilic groups. Oligonucleotides according to the invention contain one or more alkylphosphonothioate or arylphosphonothioate internucleotide linkage. In a preferred embodiment, an oligonucleotide according to the invention contains two or more alkylphosphonothioate or arylphosphonothioate internucleotide linkages at or near the 3' end of the oligonucleotide, the 5' end of the oligonucleotide, or both ends of the oligonucleotide. Oligonucleotides according to this preferred embodiment are more resistant to nucleases than are oligonucleotides that are known in the art.

In another preferred embodiment, the alkyl group of the alkylphosphonothioate internucleotide linkage is a methyl group. However, other alkyl groups that are suitable include alkyl groups having one to 7 carbon atoms, wherein the alkyl group is unsubstituted or substituted, for example, with halo, hydroxy, trifluoromethyl, cyano, nitro, acyl, acyloxy, alkoxy, carboxyl carbalkoxyl or amino groups. In addition, the aryl group of the arylphosphonothioate linkage may be unsubstituted or substituted, for example, with halo, hydroxy, trifluoromethyl, cyano, nitro, acyl, acyloxy, alkoxy, carboxyl, carbaloxyl or amino groups.

Preferably, oligonucleotides according to the invention have a nucleotide sequence that is complementary to a nucleic acid sequence that is from a virus, a pathogenic organism, or a cellular gene or gene transcript, the abnormal gene expression or product of which results in a disease state. However, oligonucleotides according to the invention having any nucleotide sequence are useful in studies of oligonucleotide stability. For purposes of the invention, the term "nucleotide sequence that is complementary to a nucleic acid sequence" is intended to mean a nucleotide sequence that hybridizes to the nucleic acid sequence under physiological conditions, e.g., by Watson-Crick base paring (interaction between oligonucleotide and single-stranded nucleic acid) or by Hoogsteen base pairing (interaction between oligonucleotide and double-stranded nucleic acid to form a triplex structure). Such hybridization under physiological conditions is measured as a practical matter by observing interference with the function of the nucleic acid sequence. Preferably, oligonucleotides according to the invention have from about 8 to about 50 nucleotides, and most preferably have from about 14 to about 35 nucleotides.

The nucleic acid sequence to which the target hybridizing region of an oligonucleotide according to the invention is complementary will vary, depending upon the disease condition to be treated. In many cases the nucleic acid sequence will be a virus nucleic acid sequence. The use of antisense oligonucleotides to inhibit various viruses is well known, and has recently been reviewed in Agrawal, Tibtech 10: 152–158 (1992). Viral nucleic acid sequences that are complementary to effective antisense oligonucleotides have been described for many viruses, including human immunodeficiency virus type I (Goodchild and Zamecnik, U.S. Pat. No. 4,806,463, the teachings of which are herein incorporated by reference.), Herpes simplex virus (U.S. Pat. No. 4,689,320, the teachings of which are incorporated herein by reference.), Influenza virus (U.S. Pat. No. 5,194,428; Ser. No. 07/516,275, allowed Jun. 30, 1992; the teachings of which are hereby incorporated by reference.) and Human papilloma virus (Storey et al., Nucleic Acids Res. 19: 4109–4114 (1991)). Sequences complementary to any of these nucleic acid sequences can be used for the target hybridizing region of oligonucleotides according to the invention, as can be nucleotide sequences complementary to nucleic acid sequences from any other virus. Additional viruses that have known nucleic acid sequences against which antisense oligonucleotides can be prepared include Foot and Mouth Disease Virus (See Robertson et al., J.

Virology 54: 651 (1985); Harris et al., J. Virology 36: 659 (1980)), Yellow Fever Virus (See Rice et al., Science 229: 726 (1985)), Varicella-Zoster Virus (See Davison and Scott, J. Gen. Virology 67: 2279 (1986), and Cucumber Mosaic Virus (See Richards et al., Virology 89: 395 (1978)).

Alternatively, the target hybridizing region of oligonucleotides according to the invention can have a nucleotide sequence complementary to a nucleic acid sequence of a pathogenic organism. The nucleic acid sequences of many pathogenic organisms have been described, including the malaria organism, *Plasmodium falciparum*, and many pathogenic bacteria. Nucleotide sequences complementary to nucleic acid sequences from any such pathogenic organism can form the oligonucleotides according to the invention.

Examples of pathogenic eukaryotes having known nucleic acid sequences against which antisense oligonucleotides can be prepared include *Trypanosoma brucei gambiense* and Leishmania (See Campbell et al., Nature 311: 350 (1984)), and *Fasciola hepatic* an (See Zurita et al., Proc. Natl. Acad. Sci. USA 84: 2340 (1987).

In yet another embodiment, oligonucleotides according to the invention can have a nucleotide sequence complementary to a cellular gene or gene transcript, the abnormal expression or product of which results in a disease state. The nucleic acid sequences of several such cellular genes have been described, including prior protein (Stahl and Prusiner, FASEB J. 5: 2799–2807 (1991)), the amyloid-like protein associated with Alzheimer's disease (U.S. Pat. No. 5,015, 570, the teachings of which are hereby incorporated by reference.) and various oncogenes and proto-oncogenes, such as c-myb c-myc, c-abl, and n-ras. Nucleotide sequences complementary to nucleic acid sequences from any of these genes can be used for oligonucleotides according to the invention, as can be nucleotide sequences complementary to any other cellular gene or gene transcript, the abnormal expression or product of which results in a disease state.

In a fourth aspect, the invention provides mixed backbone and chimeric oligonucleotides. Both mixed backbone and chimeric oligonucleotides according to the invention contain alkylphosphonothioate or arylphosphonothioate internucleotide linkages in addition to some other type of internucleotide linkage. Preferably, the other type of internucleotide linkage is selected from the group consisting of alkylphosphonate, phosphodiester, phosphotriester, phosphorothioate, phosphorodithioate, phosphoramidate, ketone, carbonate, sulfone and thioamidate linkages, or any combination of these, although other internucleotide linkages may be used as well.

For mixed backbone oligonucleotides according to the invention, the alkylphosphonothioate or arylphosphonothioate internucleotide linkages and other internucleotide linkages can be in any order within the oligonucleotide. Chimeric oligonucleotides according to the invention are similar, but have groups of nucleotides having the same internucleotide linkage type. A given group of nucleotides may have alkylphosphonothioate or arylphosphonothioate internucleotide linkages or some other type of internucleotide linkage. Such groups can be located at either the 5' or 3' end of the oligonucleotide, or may be centrally located within the oligonucleotide. The size of such groups will generally be at least 3 nucleotides (2 alkylphosphonothioate linkages) and may be much larger. In a preferred embodiment, a chimeric oligonucleotide has two groups of alkylphosphonothioate or arylphosphonothioate-linked nucleotides, one at each end. Another preferred embodiment has one such group of alkylphosphonothioate-linked nucleotides, which may be either at the 5' end or the 3' end of the oligonucleotide, and in addition has a group of 4 or more nucleotides linked by phosphodiester, phosphorothioate, or phosphorodithioate linkages.

In a fifth aspect, the invention provides a method for inhibiting the gene expression of a virus, pathogenic organism, or a cellular gene or gene transcript, the expression or product of which results in a disease state. Such inhibition is accomplished by administering an oligonucleotide according to the invention to cells that are infected by such a virus or pathogenic organism, or affected by such expression or product of a cellular gene or gene transcript, the expression or product of which results in a disease state. When such cells are in a human or animal body such administration will generally be carried out by administering the oligonucleotide orally, parenterally, topically, transdermally, or by aerosol. In such cases, such administration of oligonucleotides according to the invention provides a method of treatment for the human or animal.

The following types of conditions are among those that can be treated by the method of the invention. Oligonucleotides that inhibit the synthesis of structural proteins or enzymes involved largely or exclusively in spermatogenesis, sperm motility, the binding of the sperm to the egg or any other step affecting sperm viability may be used as contraceptives for men. Similarly, contraceptives for women may be oligonucleotides that inhibit proteins or enzymes involved in ovulation, fertilization, implantation or in the biosynthesis of hormones involved in those processes.

Hypertension can be controlled by oligodeoxynucleotides that suppress the synthesis of angiotensin converting enzyme or related enzymes in the renin/angiotensin system; platelet aggregation can be controlled by suppression of the synthesis of enzymes necessary for the synthesis of thromboxane A2 for use in myocardial and cerebral circulatory disorders, infarcts, arteriosclerosis, embolism and thrombosis; deposition of cholesterol in arterial wall can be inhibited by suppression of the synthesis of fatty acryl co-enzyme A: cholesterol acyl transferase in arteriosclerosis; inhibition of the synthesis of cholinephosphotransferase may be useful in hypolipidemia.

There are numerous neural disorders in which hybridization arrest can be used to reduce or eliminate adverse effects of the disorder. For example, suppression of the synthesis of monoamine oxidase can be used in Parkinson's disease; suppression of catechol o-methyl transferase can be used to treat depression; and suppression of indole N-methyl transferase can be used in treating schizophrenia.

Suppression of selected enzymes in the arachidonic acid cascade which leads to prostaglandins and leukotrienes may be useful in the control of platelet aggregation, allergy, inflammation, pain and asthma.

Suppression of the protein expressed by the multidrug resistance (mdr) gene, which is responsible for development of resistance to a variety of anti-cancer drugs and is a major impediment in chemotherapy may prove to be beneficial in the treatment of cancer.

Oligonucleotide sequences complementary to nucleic acid sequences from any of these genes can be used for the target hybridizing region of oligonucleotides according to the invention, as can be oligonucleotide sequences complementary to any other cellular gene or gene transcript, the abnormal expression or product of which results in a disease state.

Antisense regulation of gene expression in plant cells has been described in U.S. Pat. No. 5,107,065, the teachings of which are hereby incorporated by reference.

In addition, according to the invention the self-stabilized oligonucleotides may be administered in conjunction with other therapeutic agents, e.g., AZT in the case of AIDS.

A variety of viral diseases may be treated by the method of treatment according to the invention, including AIDS, ARC, oral or genital herpes, papilloma warts, flu, foot and mouth disease, yellow fever, chicken pox, shingles, HTLV-leukemia, and hepatitis. Among fungal diseases treatable by the method of treatment according to the invention are candidiasis, histoplasmosis, cryptococcocis, blastomycosis, aspergillosis, sporotrichosis, chromomycosis, dematophytosis and coccidioidomycosis. The method can also be used to treat rickettsial diseases (e.g., typhus, Rocky Mountain spotted fever), as well as sexually transmitted diseases caused by *Chlamydia trachomatis* or *Lymphogranuloma venereum*. A variety of parasitic diseases can be treated by the method according to the invention, including amebiasis, Chegas' disease, toxoplasmosis, pneumocystosis, giardiasis, cryptosporidiosis, trichomoniasis, and *Pneumocystis carini* pneumonia; also worm (helminthic diseases) such as ascariasis, filariasis, trichinosis, schistosomiasis and nematode or cestode infections. Malaria can be treated by the method of treatment of the invention regardless of whether it is caused by *P. falciparum, P. vivax, P. orale,* or *P. malariae*.

The infectious diseases identified above can all be treated by the method of treatment according to the invention because the infectious agents for these diseases are known and thus oligonucleotides according to the invention can be prepared, having an oligonucleotide sequence that is complementary to a nucleic acid sequence that is an essential nucleic acid sequence for the propagation of the infectious agent, such as an essential gene.

In addition, oligonucleotides according to the invention can be coadministered with other compounds for the treatment of disease. Examples of such compounds that may be coadministered with oligonucleotides according to the invention are AZT, DDI, DDC, and methotrexate.

Oligonucleotides according to the invention have many advantages over oligonucleotides that are known in the art of antisense oligonucleotide therapy. First, oligonucleotides having alkylphosphonothioate or arylphosphonothioate internucleotide linkages are resistant to nucleases, and this resistance increases with increasing numbers of alkylphosphonothioate or arylphosphonothioate linkages, especially at or near the 3' end of the oligonucleotide. Second, very great nuclease resistance is provided by even a limited number of alkylphosphonothioate or arylphosphonothioate linkages. This allows the use within the oligonucleotide of nucleotides having other types of internucleotide linkages that confer additional advantages upon the oligonucleotide as a therapeutic agent. For example, groups of four or more phosphorothioate phosphorodithioate or phosphodiester-linked nucleotides can be used, thereby allowing the oligonucleotide to activate RNase H, an important mechanism of action for therapeutic antisense oligonucleotides. In addition, the use of oligonucleotide phosphodiesters results in more stable duplex formation between the antisense oligonucleotide and the complementary target nucleic acid. A third advantage is that chimeric oligonucleotides according to the invention are even quite resistant to nucleolytic degradation and clearance in vivo, relative to oligonucleotide phosphodiesters or phosphorothioates, using the mouse model described in Agrawal and Tang, Proc. Natl. Acad. Sci. USA 88: 7597–7599 (1991) (data not shown). Finally, oligonucleotides according to the invention have the advantage of being easy to synthesize, since such synthesis requires only the incorporation of two additional steps into conventional oligonucleotide synthesis schemes.

The following examples are intended to further illustrate certain preferred embodiments of the invention, and are not intended to be limiting in nature.

EXAMPLE 1

Preparation of a Dinucleoside Methylphosphonothioate

To establish conditions for synthesizing the methylphosphonothioate internucleotide linkage, a dinucleotide containing that linkage was prepared. Synthesis was carried out as shown in FIG. 1 using thymidyl controlled pore glass (T-CPG) on 8 micromole scale and coupling was carried out with T-methylphosphonamidite, using a standard amidite coupling cycle, as described in Agrawal and Goodchild, Tet. Lett. 28: 3539–3592 (1987). After coupling, oxidative thiolation was carried out, using 1% Beaucage reagent (3H-1, 2-benzodithiole-2-one) in acetonitrile for 5 minutes at ambient temperature, to generate a CPG-bound dinucleoside methylphosphonothioate. The CPG-bound dinucleoside methylphosphonothioate was then treated with 5 ml concentrated ammonium hydroxide for 2 hours at room temperature to cleave the dinucleoside methylphosphonothioate (dinucleoside 5) from the CPG. Dinucleoside methylphosphonothioates AG(8) and AT(9) were also synthesized. For dinucleotides 8 and 9 deprotection was carried out with 1:1 ethylene diamine-ethanol for 5 hours at room temperature.

Deprotected dinucleoside 5 was then analyzed using reversed phase HPLC after removal of solvent by evaporation in vacuo. This was carried out using Buffer A (0.1M $NH_4OAc$) and Buffer B (20% Buffer A+80% $CH_3CN$) at a gradient of 0% Buffer B for 2 minutes, then 0–60% Buffer B in A+B over 30 minutes at ambient temperature in a Novapak™ $C_{18}$ cartridge with RCM 100 cartridge holder, with a flow rate of 1.5 ml per minute. The dinucleotide was detected with a 260 nm detector.

HPLC profile analysis of dinucleotide 5 showed two peaks, RT 19.97 minutes and 20.46 minutes, indicating the formation of diastereoisomers, as shown in the synthetic scheme of FIG. 1. The product was then compared with an authentic dinucleoside methylphosphonate (7), which also gave two peaks on reversed phase HPLC, with RT 15.35 minutes and 15.62 minutes, a lower retention time resulting from the lesser hydrophobicity of dinucleotide 7. Dinucleotide 8 showed two peaks, with RT 17.27 minutes and 18.36 minutes. Dinucleotide 9 showed a poorly separated doublet at RT 28.08 minutes.

The identity of the methylphosphonothioate linkage was further confirmed by $^{31}P$ NMR analysis, using a Varion Gemini 200™ spectrometer. Dinucleoside 5 gave a peak at 95.92 ppm, compared with 37.3 ppm for dinucleoside 7. This value agrees well with the reported value of 97.9 ppm for fully protected dTT containing a methylphosphonothioate linkage. (See Roelen et al., Nucleic Acids Res. 16: 7633–7645 (1988)).

EXAMPLE 2

Synthesis of Oligonucleotides Having Single Methylphosphonothioate Linkages at Various Positions The following 5-mer and 6-mer oligonucleotides were synthesized:

1. dTTTTTT [SEQ. ID NO: 1]
2. dTTTTT [SEQ. ID NO: 2]
3. dTTTTT*T [SEQ. ID NO: 3]
4. dTTT*TTT [SEQ. ID NO: 4]

For each of these oligonucleotides, the asterisks indicate the positions of methylphosphonothioate linkages, with the remainder of the internucleoside linkages being phosphodiester linkages.

Oligonucleotides 1 and 2 were synthesized using nucleoside betacyanoethylphosphoramidites on 1 micromole scale and a standard amidite coupling cycle. After each coupling, oxidation was carried out with iodine. Oligonucleotide 3 was synthesized using a first coupling of thymidine methylphosphonamidite followed by oxidation with Beaucage reagent, as described in Example 1, then further couplings were carried out using thymidine beta-cyanoethylphosphoramidites followed by iodine oxidation. Oligonucleotide 4 was synthesized using thymidine beta-cyanoethylphosphoramidite for the first two couplings, each followed by iodine oxidation, then using thymidine methylphosphonamidite for the third coupling, followed by oxidation with Beaucage reagent, and finally, thymidine beta-cyanoethylphosphoramidites for the last two couplings, followed by iodine oxidation. For each oligonucleotide, the CPG-bound oligonucleotide was deprotected after assembly, using 1:1 ethylene diamine-ethanol for 5 hours at room temperature.

The oligonucleotides were analyzed on ion exchange HPLC at ambient temperature using Buffer A (1 mM $KH_2PO_4$, pH 6.3, in 60% $HCONH_2$) and Buffer B (300 mM $KH_2PO_4$, pH 6.3, in 60% $HCONH_2$) on a Partisil SAX (Z-module) column with a gradient of 0% A for 2 minutes, then 0–20% B in A+B over 25 minutes, with a flow rate of 3 ml per minute. Oligonucleotides were detected with a 280 nm detector. Oligonucleotide 1 (a 6-mer with 5 negative charges) had a RT of 16.08 minutes. Oligonucleotides 2 (a 5-mer containing 4 negative charges) had a RT of 12.53 minutes. Oligonucleotide 3 (a 6-mer having 4 negative charges) had a RT of 12.69 minutes. Oligonucleotide 4 (a 6-mer having 4 negative charges) had a RT of 13.28 minutes.

These results demonstrate that a methylphosphonothioate linkage can be incorporated into an oligonucleotide at both terminal and internal positions, and that such linkages are stable under standard amidite assembly and deprotection conditions.

EXAMPLE 3

Synthesis of Oligonucleotides Having Multiple Methylphosphonothioate Linkages At Various Positions The following 20-mer oligonucleotides were synthesized:
5. ACACCCAATTCTGAAAATGG [SEQ. ID NO: 5]
6. ACACCCAATTCTGAAAAT*G*G [SEQ. ID NO: 6]
7. ACACCCAATTCTGAAAA*T*G*G [SEQ. ID NO: 7]
8. ACACCCAATTCTGAAA*A*T*G*G [SEQ. ID NO: 8]

For each oligonucleotide, the asterisks indicate the positions of methylphosphonothioate linkages, with all other linkages being phosphodiester linkages.

Oligonucleotide 5 was synthesized using the method described in U.S. Pat. No. 5,149,798, (Ser. No. 07/334,679; allowed on Mar. 19, 1992) followed by iodine oxidation deprotection in concentrated ammonia and standard reversed phase purification. Oligonucleotide 6 was synthesized as follows: (a) nucleoside methylphosphonamidites were used in the first two couplings; (b) the coupled nucleotide methylphosphonites were oxidized with Beaucage reagent, as described in Example 1; (c) remaining couplings were carried out using H-phosphonate chemistry, as described for oligonucleotide 5, above; (d) resulting oligonucleotide was oxidized with iodine; (e) oxidized oligonucleotide was deprotected at room temperature for 30 minutes in 0.5 ml 45:45:10 acetonitrile: aqueous ethanol: ammonium hydroxide, then by adding 0.5 ml ethylene diamine and keeping at room temperature for 6 hours with occasional stirring; (f) the mixture was filtered and evaporated in vacuo to obtain a solid mass; and (g) the mass was dissolved in water and desalted on SepPak $C_{18}$. Oligonucleotides 7 and 8 were synthesized in identical fashion, except that the method of Example 1 was used for the first 3 and 4 couplings, respectively. Purity of the oligonucleotides was confirmed using PAGE (data not shown).

These results demonstrate that multiple methylphosphonothioate linkages can be introduced into oligonucleotides at various positions, and that such linkages are stable under standard H-phosphonate assembly conditions.

EXAMPLE 4

Synthesis Of Chimeric Oligonucleotides Having Both Methylphosphonothioate and Phosphorothioate Linkages The following 20-mer oligonucleotides were synthesized:
9. ACACCCAATTCTGAAAATGG [SEQ. ID NO: 9]
10. ACACCCAATTCTGAAAAT*G*G [SEQ. ID NO: 10]
11. ACACCCAATTCTGAAAA*T*G*G [SEQ. ID NO: 11]
12. ACACCCAATTCTGAA*A*T*G*G [SEQ. ID NO: 12]

For each oligonucleotide, asterisks indicate the positions of methylphonothioate linkages, with the remaining linkages being phosphorothioate linkages.

Oligonucleotides 9–12 were synthesized in identical fashion as oligonucleotides 5–8, except that oxidation was carried out using standard $S_8$ oxidation rather than iodine oxidation to obtain phosphorothioate linkages. (See, for example Agrawal et al., Proc. Natl. Acad. Sci. USA 85: 7079–7083 (1988). Purity of the chimeric oligonucleotides was confirmed using PAGE (data not shown).

These results demonstrate that methylphosphonothioate linkages can be introduced at various positions in oligonucleotides having other artificial internucleotide linkages, in this case phosphorothioate linkages.

EXAMPLE 5

Synthesis Of Oligonucleotides Having Multiple Methylphosphonothioate Linkages At Both Ends The following 25-mer oligonucleotide was synthesized:
13. C*T*C*TCGCACCCATCTCTCTCCT*T*C*T [SEQ. ID NO: 13]

Asterisks indicate the positions of methylphosphonothioate linkages, with the remaining linkages being phosphorothioate linkages.

Oligonucleotide 13 was synthesized using the method described in Example 1 for the first three couplings, then standard amidite chemistry for the next eighteen couplings followed by oxidation with Beaucage reagent, and finally the method of Example 1 for the last three couplings. Deprotection was carried out for the DMTr-oligonucleotide as described for oligonucleotide 6 in Example 3. After deprotection, DMTr-oligonucleotide 13 was purified using $C_{18}$ low pressure liquid chromatography (LPLC). Purity of the oligonucleotide was confirmed by PAGE (data not shown).

These results demonstrate that methylphosphonothioate linkages can be selectively introduced at any position in an oligonucleotide by alternating the coupling and oxidation steps used to produce the methylphosphonothioate linkages with coupling steps used to produce other linkages, in this case phosphodiester linkages.

EXAMPLE 6

Resistance of Oligonucleotides Having Methylphosphonothioate Linkages to Nucleolytic Degradation Oligonucleotides 5–8, described in Example 3, were tested for their relative resistance to 3' exonucleolytic degradation. For each oligonucleotide, 0.4 $A_{260}$ units of oligonucleotide was lyophilized, dissolved in 0.5 ml buffer (10 mM Tris, 10 mM $MgCl_2$, pH 8.5) and mixed with 5 µl (1.5 milliunits) of snake venom phosphodiesterase. The mixture was incubated at 37° C. in a thermally regulated cell and $A_{260}$ was plotted against time. Increase in hyperchromicity was used as the indicator for oligonucleotide degradation. The results are shown in Table 1, below.

These results demonstrate that oligonucleotides having methylphosphonothioate linkages near the 3' end (oligonucleotides 6–8) were far more stable than the oligonucleotide lacking such linkages. In addition, oligonucleotide stability increased with increasing numbers of methylphosphonothioate linkages (4 linkages>>3 linkages>2 linkages).

TABLE 1

RESISTANCE OF OLIGONUCLEOTIDES TO NUCLEOLYTIC DEGRADATION

| Oligonucleotide | t½ (seconds) | % increase in hyperchromicity |
| --- | --- | --- |
| Oligonucleotide 5 | 44 | 22.56 |
| Oligonucleotide 6 | 210 | 24.58 |
| Oligonucleotide 7 | 264 | 18 |
| Oligonucleotide 8 | 401 | 15.54 |

EXAMPLE 7

Duplex Stability of Oligonucleotides Having Methylphosphonothioate Linkages

The stability of duplexes between oligonucleotides having methylphosphonothioate linkages and complementary oligodeoxynucleotides was tested in the following manner. Oligonucleotides 9, 10, 11 and 12 (0.2 $A_{260}$ units) were mixed with equal amounts of complementary oligodeoxynucleotide phosphodiester in 1 ml of buffer (100 mM NaCl) containing 10 mM $Na_2HPO_4$, pH 7.4). The mixtures were heated to 70° C., then cooled to 20° C. at a rate of temperature change of 2° C./minute. The mixtures were then reheated from 20° C. to 80° C. at a rate of temperature change of 1° C./minute, an hyperchromicity at $A_{260}$ was recorded as a function of temperature. The results are shown in FIG. 5. Generally, the change in hyperchromicity was about 22%. Oligonucleotides containing increasing numbers of methylphosphonothioate linkages showed a decreased in $T_m$ of about 1–2° C. for each linkage.

EXAMPLE 8

Anti-HIV Activity of Methylphosphonothioate-Containing Oligonucleotides

The ability to inhibit HIV-1 in tissue culture was tested for oligonucleotide phosphorothioates having methylphosphonothioate linkages at their 3' ends (chimeric oligonucleotides) or lacking such methylphosphonothioate linkages. Oligonucleotides 9, 10 and 11 were used for this study. All three oligonucleotides have a nucleotide sequence homologous to the HIV-1 gag gene.

H9 lymphocytes were infected with HIV-1 virions (0.01–0.1 $TCID_{50}$/cell) for one hour at 37° C. After one hour, unadsorbed virions were washed and the infected cells were divided among wells of 24 wellplates. To the infected cells, an appropriate concentration (from stock solution) of oligonucleotide was added to obtain the required concentration in 2 ml medium. The cells were then cultured for three days. At the end of three days, infected cells were examined visually for syncytium formation or stained with trypan blue for cytopathic effect determination. The results are shown in Table 2, below.

These results demonstrate that both of the methylphosphonothioate-containing oligonucleotides had some increase in efficacy in decreasing syncytium formation and reduction of cytopathic effect. Both oligonucleotides had in vitro effective dosages similar to that of oligonucleotide 9 (oligonucleotide phosphorothioate). In view of the fact that oligonucleotides 10 and 11 are stable in animals, whereas oligonucleotide 9 is not (data not shown), these results suggest that chimeric oligonucleotides containing methylphosphonothioate internucleotide linkages should have greater in vivo efficacy than oligonucleotides phosphorothioates.

TABLE 2

ANTI-HIV EFFECT OF OLIGONUCLEOTIDES

| | Conc. µg/ml | Avg. No. of Syncytia | % Reduct. in CPE | $ED_{50}$ µg/ml |
| --- | --- | --- | --- | --- |
| Oligonucleotide 9 | 0.32 | 150 | 2 | 2.45 |
| | 1.0 | 156 | 0 | |
| | 3.2 | 53 | 65 | |
| | 10 | 0 | 100 | |
| | 32 | 0 | 100 | |
| | 100 | 0 | 100 | |
| Oligonucleotide 10 | 0.32 | 138 | 10 | 2.79 |
| | 1.0 | 133 | 13 | |
| | 3.2 | 69 | 55 | |
| | 10 | 0 | 100 | |
| | 32 | 0 | 100 | |
| | 100 | 0 | 100 | |
| Oligonucleotide 11 | 0.32 | 135 | 12 | 2.02 |
| | 1.0 | 130 | 15 | |
| | 3.2 | 42 | 73 | |
| | 10 | 0 | 100 | |
| | 32 | 0 | 100 | |
| | 100 | 0 | 100 | |

We claim:

1. An antisense oligonucleotide having from about 8 to about 50 nucleotides, wherein three or more, but not all, nucleosides are connected by methylphosphonothioate linkages, wherein the sulfur of the methylphosphonothioate linkage is a non-bridging atom.

2. The oligonucleotide according to claim 1, wherein the nucleosides that are connected by a methylphosphonothioate linkage comprise the most 5' nucleosides.

3. The oligonucleotide according to claim 1, having a nucleotide sequence that is complementary to a nucleic acid sequence that is from a virus, a pathogenic organism, or a cellular gene or gene transcript, the expression of which results in a disease state.

4. The oligonucleotide according to claim 1, further comprising one or more ribose or deoxyribose nucleosides having an alkylphosphonate, phosphodiester, phosphotriester, phosphorothioate, phosphorodithioate, phosphoramidate, ketone, sulfone, carbonate, or thioamidate internucleoside linkage.

5. The oligonucleotide according to claim 1, wherein the nucleosides connected by methylphosphonothioate linkages are the 3'-most nucleosides.

6. An antisense oligonucleotide having from about 8 to about 50 nucleotides, wherein two or more, but not all, nucleosides are connected by an alkylphosphonothioate or arylphosphonothioate linkage wherein the sulfur of the alkylphosphonothioate or arylphosphonothioate linkage is a non-bridging atom.

7. The oligonucleotide according to claim 6, wherein the nucleotides that are connected by an alkylphosphonothioate or arylphosphonothioate linkage comprise the most 3' and the most 5' oligonucleotides.

8. The oligonucleotide according to claim 6, wherein the alkyl group of the alkylphosphonothioate or arylphosphonothioate linkage is selected from the group consisting of unsubstituted alkyl groups having 1–5 carbon atoms, and alkyl groups having 1–5 carbon atoms and being substituted with halo, hydroxy, trifluoromethyl, cyano, nitro, acyl, acyloxy, alkoxy, carboxyl, carbalkoxy or amino groups, and combinations thereof.

9. The oligonucleotide according to claim 6, wherein the aryl group of the arylphosphonothioate is an unsubstituted aryl group or an aryl group substituted with halo, hydroxy, trifluoromethyl, cyano, nitro, acyl, acyloxy, alkoxy, carboxyl, carbalkoxy or amino groups, and combinations thereof.

10. An oligonucleotide according to claim 6, further comprising one or more ribose or deoxyribose nucleosides having an alkylphosphonate, phosphodiester, phosphotriester, phosphorothioate, phosphorodithioate, phosphoramidate, ketone, sulfone, carbonate, or thioamidate internucleoside linkage.

11. An antisense oligonucleotide having the nucleotide sequence 5'-ACACCCAATTCTGAAAATGG-3', wherein the two most 3' internucleotide linkages are methylphosphonothioate linkages, and wherein all other internucleotide linkages are phosphorothioate linkages.

12. An antisense oligonucleotide having the nucleotide sequence 5'-ACACCCAATTCTGAAAATGG-3', wherein the three most 3' internucleotide linkages are methylphosphonothioate linkages, and wherein all other internucleotide linkages are phosphorothioate linkages.

13. A method of incorporating into an antisense oligonucleotide an alkyl- or aryl-phosphonothioate internucleoside linkage, the method comprising the steps of (a) coupling together two nucleosides via an alkyl- or aryl-phosphonite linkage; and (b) oxidatively thiolating the alkyl- or aryl-phosphonite linkage with 3H-1,2-benzodithiol-3-one-1,1-dioxide to produce an alkyl or aryl-phosphonothioate linkage, wherein said coupling and thiolating steps are conducted on a solid support and the sulfur of the alkyl or aryl-phosphonothioate linkage is a non-bridging atom.

14. The method according to claim 13 wherein the alkyl- or aryl-moiety is methyl.

15. A method of making an antisense oligonucleotide having one or more alkyl- or aryl-phosphonothioate linkages at its 3' end, the method comprising the steps of:
    (a) coupling together two nucleosides via an alkyl- or aryl-phosphonite linkage;
    (b) oxidatively thiolating the alkyl- or aryl-phosphonite linkage with 3H-1,2-benzodithiol-3-one-1,1-dioxide to produce an alkyl- or aryl-phosphonothioate linkage;
    (c) repeating steps (a) and (b) for each additional alkyl- or aryl-phosphonothioate linkage to be added; and
    (d) sequentially adding as many nucleotides as desired in additional coupling steps, wherein said coupling and thiolating steps are conducted on a solid support and the sulfur of the alkyl or aryl-phosphonothioate linkage is a non-bridging atom.

16. The method according to claim 15 wherein the alkyl- or aryl-moiety is methyl.

17. A method of making an antisense oligonucleotide having one or more alkyl- or aryl-phosphonothioate linkages at its 5' end, the method comprising the steps of:
    (a) sequentially coupling together as many nucleotides as desired;
    (b) sequentially adding two nucleosides coupled together via an alkyl- or aryl-phosphonite linkage;
    (c) oxidatively thiolating the alkyl- or aryl-phosphonite linkage with 3-H-1,2-benzodithiol-3-one-1,1-dioxide to produce a alkyl- or aryl-phosphonothioate linkage; and
    (d) repeating steps (b) and (c) for each additional alkyl- or aryl-phosphonothioate linkage to be added, wherein said coupling and thiolating steps are conducted on a solid support and the sulfur of the alkyl or aryl-phosphonothioate linkage is a non-bridging atom.

18. The method according to claim 17 wherein the alkyl- or aryl-moiety is methyl.

19. A method of making an antisense oligonucleotide having one or more alkyl- or aryl-phosphonothioate linkages at its 5' and 3' ends, the method comprising the steps of:

(a) coupling together two nucleosides via a alkyl- or aryl-phosphonite linkage;

(b) oxidatively thiolating the alkyl- or aryl-phosphonite linkage with 3H-1,2-benzodithiol-3-one-1,1-dioxide to produce a alkyl- or aryl-phosphonothioate linkage;

(c) repeating steps (a) and (b) for each additional alkyl- or aryl-phosphonothioate linkage to be added; and (d) sequentially adding as many nucleotides as desired in additional coupling steps;

(e) sequentially adding two nucleosides coupled together via an alkyl- or aryl-phosphonite linkage;

(f) oxidatively thiolating the alkyl- or aryl-phosphite linkage with 3H-1,2-benzodithiol-3-one-1,1-dioxide to produce an alkyl- or aryl-phosphonothioate linkage; and (g) repeating steps (e) and (f) for each additional alkyl- or aryl-phosphonothioate to be added, wherein said coupling and thiolating steps are conducted on a solid support and the sulfur of the alkyl or aryl-phosphonothioate linkage is a non-bridging atom.

20. The method according to claim 19 wherein the alkyl- or aryl-moiety is methyl.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 6 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

TTTTTT    6

(2) INFORMATION FOR SEQ ID NO:2:

(i) SEQUENCE CHARACTERISTICS:
      (A) LENGTH: 5 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

TTTTT    5

(2) INFORMATION FOR SEQ ID NO:3:

(i) SEQUENCE CHARACTERISTICS:
      (A) LENGTH: 6 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

TTTTTT    6

(2) INFORMATION FOR SEQ ID NO:4:

(i) SEQUENCE CHARACTERISTICS:
      (A) LENGTH: 6 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

TTTTTT                                                                                             6

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:5:

ACACCCAATT CTGAAAATGG                                                                              20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:6:

ACACCCAATT CTGAAAATGG                                                                              20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:7:

ACACCCAATT CTGAAAATGG                                                                              20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:8:

ACACCCAATT CTGAAAATGG                                                                              20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:9:

ACACCCAATT CTGAAAATGG                                                20

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:10:

ACACCAATTC TGAAAATGG                                                 19

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:11:

ACACCCAATT CTGAAAATGG                                              20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:12:

ACACCCAATT CTGAAAATGG                                              20

(2) INFORMATION FOR SEQ ID NO:13:

(i) SEQUENCE CHARACTERISTICS:
        (A) LENGTH: 25 base pairs

```
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:13:

CTCTCGCACC CATCTCTCTC CTTCT                                              25
```